(12) United States Patent  
Almo (10) Patent No.: US 6,308,875 B1
(45) Date of Patent: Oct. 30, 2001

(54) SURGICAL INSTRUMENT STORAGE PACK (75) Inventor: Kristi M Almo, Seattle, WA (US)

(73) Assignee: Kristi M. Almo, Seattle, WA (US)

( * ) Notice: Subject to any disclaimer, the term of this patent is extended or adjusted under 35 U.S.C. 154(b) by 0 days.

(21) Appl. No.: 09/372,519

(22) Filed: Aug. 11, 1999

(51) Int. Cl.[7] ..................................................... A45F 5/02
(52) U.S. Cl. .................................. 224/660; 2/94; 2/251; 2/253; 206/370; 206/439; 383/11; 383/38; 383/39; 383/33; 224/223; 224/681
(58) Field of Search ..................... 128/80, 402; 190/109; 150/52, 112, 114, 116; 224/5, 223, 680, 681, 682, 684; 206/63.3, 363, 370, 439; 383/11, 38, 39, 33; 2/94, 251, 253

(56) References Cited

U.S. PATENT DOCUMENTS

| | | | |
|---|---|---|---|
| 2,697,465 | * 12/1954 | Johnson | 383/39 |
| 2,873,781 | * 2/1959 | Langley | 383/39 |
| 3,589,595 | * 6/1971 | White | 383/33 |
| 4,041,549 | * 8/1977 | Atkinson | 2/94 |
| 4,057,144 | * 11/1977 | Schuster | 206/439 |
| 4,196,245 | * 4/1980 | Kitson et al. | 428/198 |
| 4,705,171 | * 11/1987 | Eldridge | 206/438 |
| 4,874,090 | * 10/1989 | Dyke | 206/439 |
| 4,936,456 | * 6/1990 | Bell et al. | 206/439 |
| 4,953,765 | * 9/1990 | Little et al. | 383/4 |
| 5,022,521 | * 6/1991 | Kane | 383/39 |
| 5,024,361 | * 6/1991 | Flowers | 224/223 |
| 5,036,866 | 8/1991 | Eldrige, Jr. et al. | |
| 5,082,111 | 1/1992 | Corbitt, Jr. et al. | |
| 5,340,550 | * 8/1994 | Johnsen et al. | 422/292 |
| 5,351,822 | 10/1994 | Sinn . | |
| 5,465,425 | * 11/1995 | Crispin | 2/102 |
| 5,549,388 | 8/1996 | Wilkes . | |
| 5,843,556 | * 12/1998 | Levas | 428/99 |
| 5,867,825 | * 2/1999 | Scheerer | 2/69 |
| 6,067,803 | * 5/2000 | Wolsey et al. | 383/4 |

OTHER PUBLICATIONS

3M Innovation Network, Global Information Web Page, http://www.mmm.com, Access date: Aug. 20, 1998, 36 pages.

* cited by examiner

Primary Examiner—Stephen P. Garbe
(74) Attorney, Agent, or Firm—Townsend and Townsend and Crew, LLP (57) ABSTRACT A surgical instrument storage pack is provided to accommodate standard or videoscopic surgical instruments. The instrument pack is removably mounted adjacent a surgeon's or surgical assistant's abdominal or chest area and incorporates pockets that are adapted to securely and removably receive surgical instruments of different shapes and sizes. The pack may be mounted by a belt with straps or other mounting mechanism to encircle or embrace the surgeon's abdomen or chest. Alternatively the pack may be mounted by other affixing elements such as adhesive strips that directly affix the pack to the abdominal or chest region of a surgical garment. In this manner, the pack is secured at a frontal abdominal or chest position of the surgeon to provide ready access to instruments placed within the pouch and to secure the pack and instruments reliably within a sterile operating field.

27 Claims, 7 Drawing Sheets

SURGICAL INSTRUMENT STORAGE PACK

BACKGROUND OF THE INVENTION

During standard surgical procedures, the surgeon requires access to and use of a large number and variety of instruments, such as scalpels, scissors, hemostats, cautery devices, suction tools, etc. In the conventional operating theater, the surgeon's access to these instruments depends largely on the surgical assistant. The assistant typically stages the instruments on a Mayo stand and one or more back tables, and delivers them to the surgeon as requested. After a task involving a particular subject instrument is completed, the assistant retrieves the instrument until it is called for again. This basic methodology has long been established and still remains in wide use, even though it presents a number of drawbacks.

The fidelity of interactions between the surgeon and surgical assistant depends to a large extent on the skill and training of the assistant. The assistant must respond promptly and accurately to the surgeon's requests in order to avoid delays and disruptions that may affect the surgeon's concentration and efficient execution of ongoing procedures. Experienced assistants should generally be able to anticipate which instruments may be requested at particular stages in an operation. The experienced assistant also knows which instruments are used in conjunction with other instruments, and which instruments require special handling or preparation before they are delivered to the surgeon. By virtue of such experience, the well-trained assistant can efficiently stage and handle instruments, with minimal delays and distraction to the surgeon.

Unfortunately, the amount of experience and ability among surgical assistants varies considerably. Many assistants are unfamiliar with certain procedures and thus fail to present desired instruments in an organized and timely manner. As a result, surgical procedures may be disrupted by delays and miscommunications involving instrument transfer. All too commonly, the surgeon's focus is drawn away from the operating field to direct activities of the assistant. At other times, inexperienced assistants will hand a surgeon the wrong instrument, either because the surgeon's instructions were misunderstood or the assistant improperly second-guessed the surgeon's needs. Often, instruments that are used repeatedly for a given procedure are retrieved and put away, even though the surgeon needs them back expediently. Other assistants leave instruments on the Mayo stand or operating field in a disorganized clutter, slowing delivery to the surgeon and creating additional confusion in the operating theater.

In addition to the lack of consistent training among surgical assistants, each doctor and assistant develops a unique working style and communication habits that can further complicate instrument transfer in the operating theater. Individual surgeons may select different operating procedures and instruments to achieve similar tasks, such that an assistant who is unfamiliar with a particular surgeon's preferences may be confused and inefficient at instrument transfer. This factor is especially significant in larger medical communities where doctors may practice in numerous hospitals and with a large number of different assistants. In this context, the fidelity of instrument transfer during operating procedures varies substantially, not only in accordance with the assistant's training but also in accordance with the degree of familiarity between the surgeon and assistant.

Other factors which complicate instrument transfer during surgical procedures include the varying demands placed on the assistant. For example, many complex operations involve multiple surgeons, each relying on a single assistant for instrument delivery and retrieval. For coronary artery bypass grafting, aortoiliac or femoropopliteal bypass grafting, complex burn and plastic reconstructions, and abdominal perineal resections, two surgeons typically operate simultaneously on two separate areas of the patient's body and call for support from one assistant. The assistant must transit between both surgeons and attend to their instrument needs in a timely and accurate fashion. During other procedures, the surgical assistant may be assigned additional tasks besides instrument handling. For example, assistants are commonly called upon to hold retractors, suction tools and other instruments in place while the surgeon proceeds with an operation. At other times, the assistant is asked to use one or both hands to help in some way with an operation. In these instances, the assistant may be unable to reach the Mayo stand or back table while performing the secondary task.

Other difficulties involved in instrument transfer during surgery arise from the required positioning of the patient, doctor and assistant during particular operations. For example, in many operations involving the genitourinary tract, anus, and perineum, the assistant and Mayo stand are both positioned behind the surgeon with the patient in a lithotomy position and the surgeon standing or seated between the patient's legs. Common examples of operations staged in this manner include total vaginal hysterectomy, radical perineal prostatectomy, cystourethroscopy, hysteroscopy, and transanal procedures. Under these circumstances, instruments are not readily transferred to the surgeon by the surgical assistant, who must avoid handing tools over the surgeon's shoulder or below waist level to maintain sterility. Likewise, returning instruments within the sterile field between a seated surgeon and standing assistant is challenging and inefficient, especially when the same instrument will be needed again shortly after it is returned.

To circumvent the foregoing difficulties that attend surgical instrument handling in the operating theater, many surgeons maintain increased control over their instruments. This is particularly true in the case of instruments that are used frequently but not continuously during a procedure, where the surgeon does not want spend the time and effort necessary to return, and shortly thereafter retrieve, the same instrument. Often, such tools which are used repeatedly, for example, a Bovie cautery, suction tool, dissecting forceps, Metzenbaum scissors or hemostat, are not relinquished to the assistant but are held or placed close at hand by the surgeon. Holding on to an instrument in this manner can impede the surgeon's concentration and dexterity. Other problems arise if the surgeon elects to place an instrument close at hand, which often involves placement of the instrument on a sterile drape covering the patient's head, chest, abdomen, or lower extremity. Such tenuous placement of instruments may result in confusion and delays for both the surgeon and the assistant which can be exacerbated by the differing positions of patients in different procedures (e.g., supine, prone jackknife, lateral decubitus, lithotomy, rotated, or other). In all patient positions, unattended instruments can endanger the patient who lies unseen beneath the drapes, can fall out of the sterile field, or be forgotten by the surgeon who then requests tools from the assistant who cannot find or retrieve them.

Various devices and methods have been proposed to facilitate instrument handling in the operating theater. Among these methods and devices, some are intended to provide the surgeon with increased control over instrument access and relieve the surgical assistant of instrument handling demands. Thus, U.S. Pat. No. 4,665,566, issued to Garrow on May 19, 1987, discloses an instrument retaining device which is a strap-like clamp for securing instruments within the surgeon's reach during an operation. The device is primarily adapted for securing tubes and requires mounting of the straps around an available surface. Thus, use of the device is primarily limited to circumstances where an extremity of the patient or other object is conveniently available to secure the straps around. Moreover, the device is not particularly well adapted to secure other instruments that are more typically desired to be left in the surgeon's control.

Other designs which have been proposed for retaining surgical instruments within reach of the surgeon include various pouch-like receptacles that are affixed, or attachable to, a surface within the operating theater to secure instruments without the need of mounting straps. Exemplifying such designs is an instrument pouch marketed by the 3M company under the name "Steri-Drape." This pouch is designed to attach by adhesive strips to the exterior of a surgical drape placed over the patient. The pouch has pockets to receive instruments and is provided as a disposable unit. An alternative design offered by 3M is a surgical drape to which are affixed multiple instrument pouches for the surgeon to secure and access instruments during an operation.

Yet additional designs incorporate removably attachable pouches that are designed to mount on a patient's body or surgical drape covering the patient's body. For example, U.S. Pat. No. 5,081,111, issued to Corbit, Jr., et al. on Jan. 21, 1992, discloses a disposable instrument pouch with receptacles and closable flaps to secure instruments that can be attached adhesively to a patient's body or surgical drape. Similarly, U.S. Pat. No. 5,036,866, issued to Eldrige, Jr., et al. on Aug. 6, 1992, discloses an instrument pouch attachable to a surgical drape by specially-designed tab that interlocks with a slot on the surgical drape. The pouch has planar walls spaced apart by a ridge and is designed with perforations to allow sterilization and re-use.

Each of the foregoing devices suffer similar drawbacks in terms of their common designs for attachment to a patient or other surface. These surfaces are limited in the operating theater and frequently change between operations—based on such changing factors as patient positioning and varying placement and configuration of operating equipment, etc. In this context, the changing location and positioning of the instrument retainer can lead to difficulties in locating and handling instruments. Such tenuous placement of instruments in the surgical field does not provide adequate security to prevent against movement or dropping of instruments outside the sterile field (i.e., between the surgeon's clavicles and the surface of the operating table). Moreover, attachment of instruments, particularly heavy or sharp instruments, to a thin drape covering the patient is ill-advised in the context of patient comfort and safety. Likewise, fixation of an instrument pouch to a particular stationary object within the operating field limits the surgeon's mobility by dictating placement of the surgeon to access the stored instruments. Finally, the pouch designs and mounting configurations of these previously proposed instrument retaining devices are not conducive to storage and retrieval of larger and more cumbersome instruments associated with the rapidly growing discipline of laparoscopic surgery.

Thus, a clear need remains in the art for a surgical instrument storage device that will facilitate instrument control and retrieval by the surgeon, free the surgical assistant from excessive instrument handling tasks, and reduce clutter and confusion in the surgical theater.

A related need exists for a surgical instrument storage device that will allow the surgeon to securely store a number of surgical instruments having a wide range of sizes and shapes, and to quickly and accurately retrieve them.

An additional need remains in the art for a surgical instrument storage device that will allow for repetitive storage and retrieval of instruments during operations while the device is situated securely within the sterile field to avoid contamination.

Another need remains in the art for a surgical instrument storage device that is adaptable for use within a wide range of surgical settings and procedures.

Yet an additional need remains in the art for a surgical instrument storage device that is economical to manufacture and use, and which is disposable or sterilizable to accommodate safe surgical practices.

SUMMARY OF THE INVENTION

The present invention fulfills the foregoing needs and satisfies other objects and advantages by providing a novel surgical instrument storage device designed to be removably mounted on a body or garment (e.g., a textile or paper surgical gown) of a surgeon or surgical assistant. The device is in the form of a pack that defines one or more pockets for secure receipt and storage of surgical instruments. Each pocket is specially designed to receive one or more instruments through an opening that permits ready insertion of the instrument into the pocket and ready retrieval of the instrument therefrom.

In one embodiment of the invention, an instrument pack (InstruPak™) is provided which is designed to accommodate standard surgical instruments, for example, hemostats, scissors and the like. The instruments may be of different shapes and sizes, and the pocket(s) of the instrument pouch may be fixed in depth or adjustable to more closely adapt the pocket(s) to longer or shorter instruments.

In one aspect, the instrument pack is removably mounted to the surgeon's abdominal area in the manner of a belt having straps or other closure means that encircle or embrace the surgeon's abdomen. Thus, the pack is secured at a frontal abdominal position of the surgeon for ready access to instruments placed within the pouch and to secure the pack and instruments reliably within a sterile operating field.

In an alternate aspect, the instrument pack is secured to a frontal abdominal or chest region of the surgeon by a sling or other harness means that may engage the surgeon's abdomen, chest, neck and/or shoulder(s).

In another alternate aspect, the pack is secured to a frontal abdominal or chest region of the surgeon without straps or sling elements by removable attachment means which affix the pack to the chest or abdominal region of a surgeon's garment, for example an adhesive material affixed to a back surface of the pack, or an engaging element that engages a complementary engaging element on the surgical garment. In more detailed aspects, the adhesive material is an adhesive gel that firmly but removably engages a frontal surface of a surgical garment. In other detailed embodiments, the removable attachment means comprise complementary engaging elements, for example snaps, buckles, or opposing segments of hook and loop material, affixed to opposing surfaces of the pack and surgical garment.

In yet another embodiment of the invention, a specialized videoscopic instrument pack (Long-InstruPak™) is provided which is designed to accommodate elongated videoscopic, e.g., laparoscopic, endoscopic and thoracoscopic, surgical instruments. The videoscopic instrument pack defines one or more pockets for secure receipt and storage of videoscopic instruments. Each pocket is specially designed to receive one or more videoscopic instruments through an opening that permits ready insertion of the instrument into the pocket and ready retrieval of the instrument therefrom. As with the standard instrument pack, the videoscopic instrument pack may be removably mounted to the surgeon's abdominal or chest area in the manner of a belt, sling, harness or other mounting mechanism to secure the pack at a frontal abdominal position for ready access to the instruments. Alternatively, the pack can be secured to the frontal abdominal or chest region of a surgeon's garment by adhesive or other engaging elements such as snaps, buckles, or opposing segments of hook and loop material.

In more detailed aspects, the videoscopic instrument pack has front and back panels that define one or more V-shaped pockets to securely and easily receive and store videoscopic instruments. The front and back panels are joined at vertical seams that are oriented downwardly toward a midline axis of the pocket. Thus, videoscopic instruments that typically have a narrow tip and wider gripping end, often including a handle or other control element, are readily accommodated within the pocket and securely engaged therein. In other detailed aspects, the pocket or pockets of the videoscopic instrument pack are themselves oriented transversely away from a midline axis of the pack, whereby the tip of an instrument stored in the pocket extends downwardly transverse away from a midline of a surgeon wearing the pack with the gripping end of the instrument situated close to the midline to facilitate storage and retrieval of the instrument.

In other detailed aspects of the invention, the surgical instrument storage device is alternatively provided with a pleated, convex pocket design to facilitate instrument insertion and retrieval. Alternatively, the front top edge of each pocket may be reinforced with a double layer of material, which optionally encloses a durable interfacing and/or a short flexible stay, to add stiffness and stability to the pocket opening. The front top edge of each pocket is preferably positioned slightly below the top edge of the back panel (see below) to facilitate instrument placement and retrieval. The pocket(s) is/are accessible with either the right or left hand and can optionally be adjusted to an approximate height of specific instruments in use. In addition, each pocket is preferably sized and dimensioned to hold instruments at an angle to the midline of the pack and surgeon's body, to facilitate storage and retrieval and minimize interference of the instruments with the surgeon's visual field and movements. The depth and width of the pocket(s) accommodate the most frequently used tools in every surgical operation, irrespective of surgical subspecialty, and can accommodate a surplus of identical or varied instruments, for example multiple clamps to facilitate such repetitive processes as clamping and dividing across a large bowel mesentery during a colectomy. The pack is preferably detachable from the surgical garment and/or the pocket(s) designed to be opened, e.g., by separation of the front and back panels, for ease of disposal or sterilization.

The present invention thus provides for greatly improved efficiency of instrument handling in the operating theater. A standard or videoscopic instrument pack worn by a surgeon or surgical assistant makes the surgeon or assistant more mobile and efficient at instrument retrieval and facilitates concentration and execution of surgical procedures. The instrument pack eliminates the need for a surgeon to verbally request certain tools. In addition, instruments which are used repetitively but not continuously used throughout an operation, for example a Bovie cautery, suction tool, dissecting forceps, Metzenbaum scissors, hemostat, can be stored in the surgeon's instrument pack and put to use as needed without any requirement for secondary assistance. The instrument pack of the invention reclaims the lost time required for a surgeon to recall the name of a desired tool, speak a request for the tool, and receive the tool from the surgical assistant who must mentally process the request and correctly locate and transfer the instrument. The surgeon thus maintains greater attention on the surgical field for a more significant amount of uninterrupted time, particularly when commonly used tools are stored within the instrument pack. In addition to these advantages, sterile surgical procedures that take place with little or no participation by a surgical assistant, for example in an outpatient office setting, in a hospital patient room, as well as in the emergency room, are greatly facilitated by use of an instrument pack as disclosed herein.

DESCRIPTION OF THE SPECIFIC EMBODIMENTS

The instant invention is directed to a surgical instrument storage device that is specially designed for removably mounting to a body or garment of a surgeon or surgical assistant to provide ready access to surgical instruments without the need for conventional instrument handling assistance by a second party. As disclosed herein, the device is a versatile tool for instrument storage and retrieval during surgical procedures that overcomes long-standing problems related to instrument handling in the surgical theater.

Figure 1:
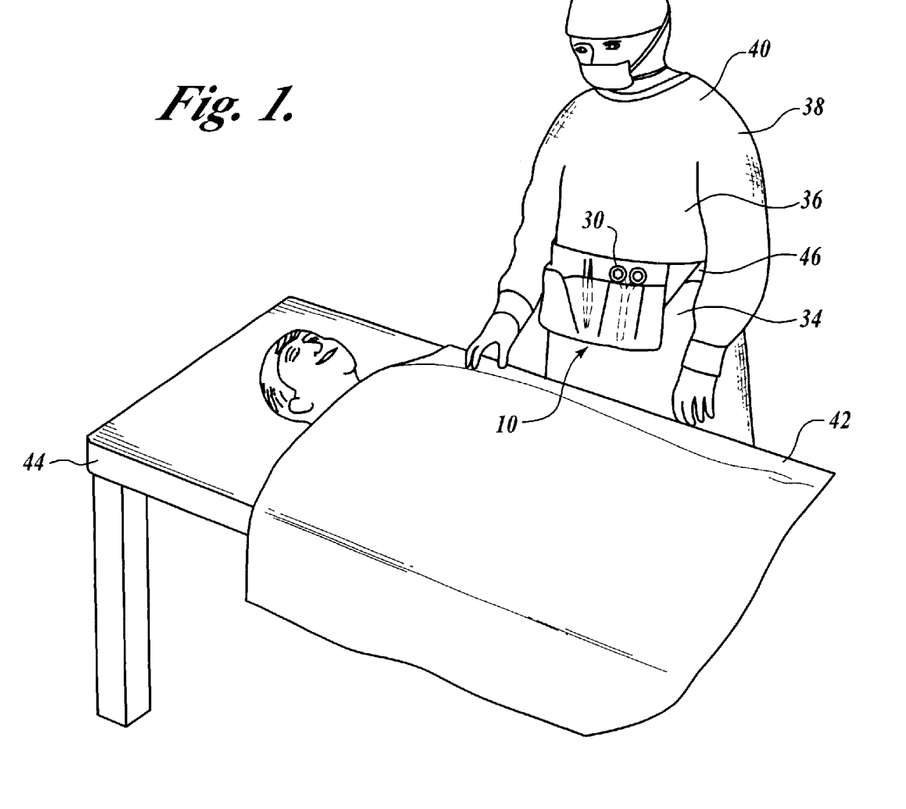
FIG. 1 is an environmental view showing a surgeon wearing a surgical instrument storage pack employing the concepts of the invention and mounted by an optional belt design.
Figure 2:
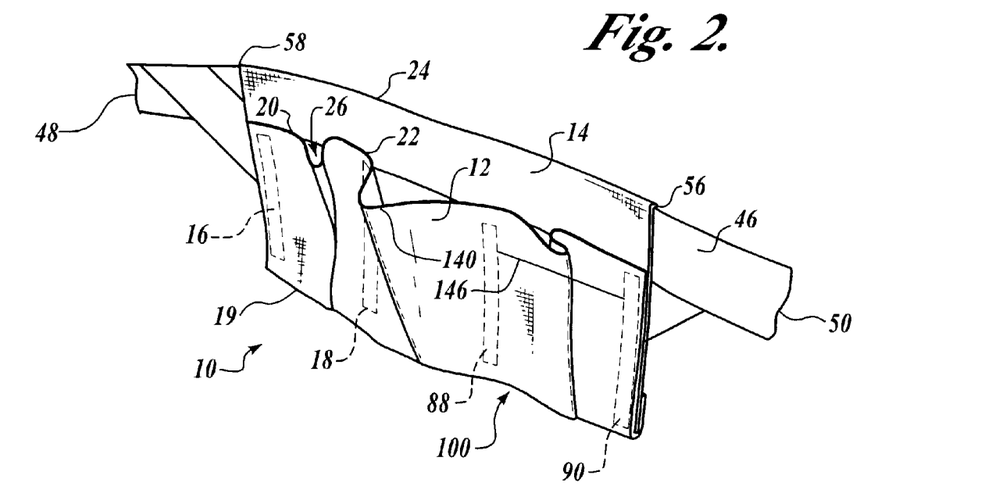
FIG. 2 is a frontal perspective view of a surgical instrument storage pack employing the concepts of the invention and mounted by an optional belt design.
Figure 3:
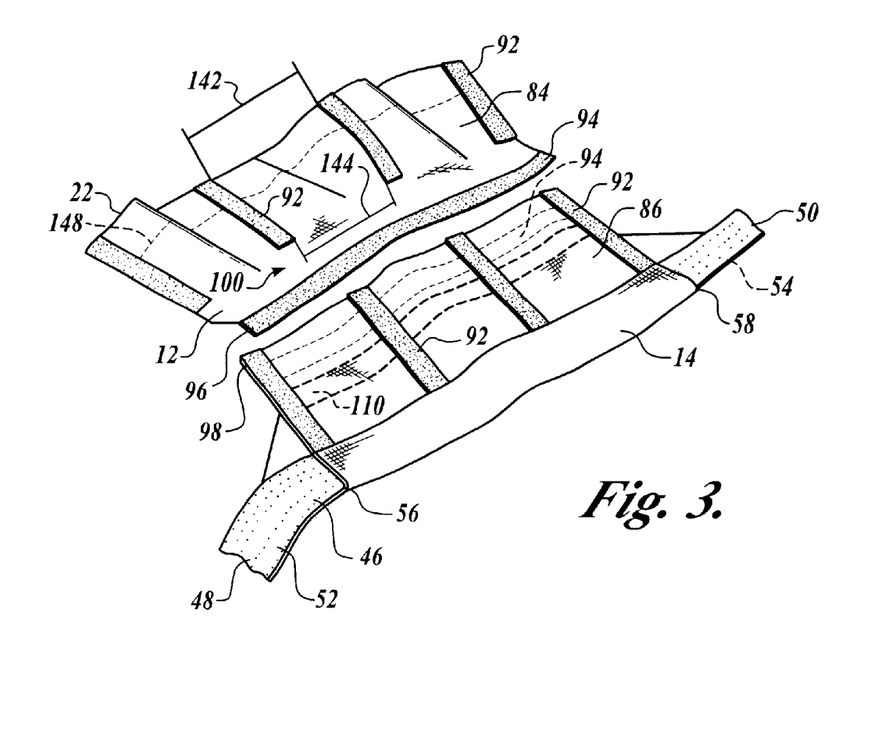
FIG. 3 is an exploded perspective view of the surgical instrument pack shown in FIG. 2.

As illustrated in FIGS. 1–3, a preferred embodiment of the invention is a storage pack 10 (InstruPak™) for standard surgical instruments. Such instruments include, but are not limited to, tonsils, scissors, hemostats, cautery devices, suction tools dissecting forceps, and the like. Thus, the instruments that may be stored within the instrument pack may be of a variety of shapes and sizes.

The instrument storage pack 10 incorporates a front panel 12 and a back panel 14 that are permanently or detachably joined along at least a first vertical seam 16 and a second vertical seam 18 and along a bottom seam 19 that together define at least one instrument-retaining pocket 20. The front and back panels have opposing upper margins, 22, 24 that collectively define a pocket opening (arrow 26). The pocket and pocket opening are specifically sized and dimensioned to removably receive and securely store one or more surgical instruments. The upper margin of the back panel is slightly elevated above the upper margin of the front panel (see, e.g., FIGS. 2 and 10) to facilitate instrument insertion which preferably involves a rearward insertion movement so that the tip of the instrument impinges against the elevated back panel and is thereby guided into the pocket without resistance by impinging against one or the other upper margins.

Figure 5:
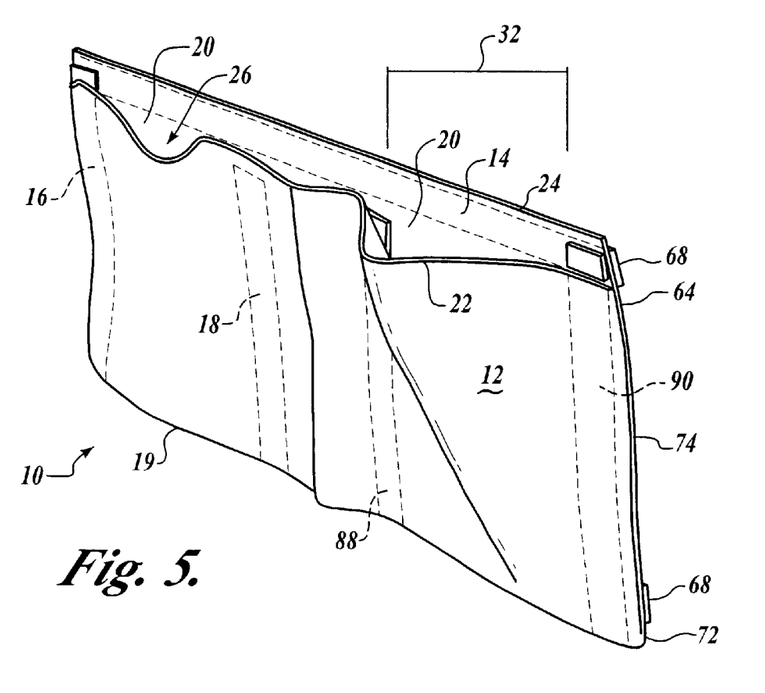
FIG. 5 is a frontal perspective view of the surgical instrument pack shown in FIG. 4.
Figure 6A:
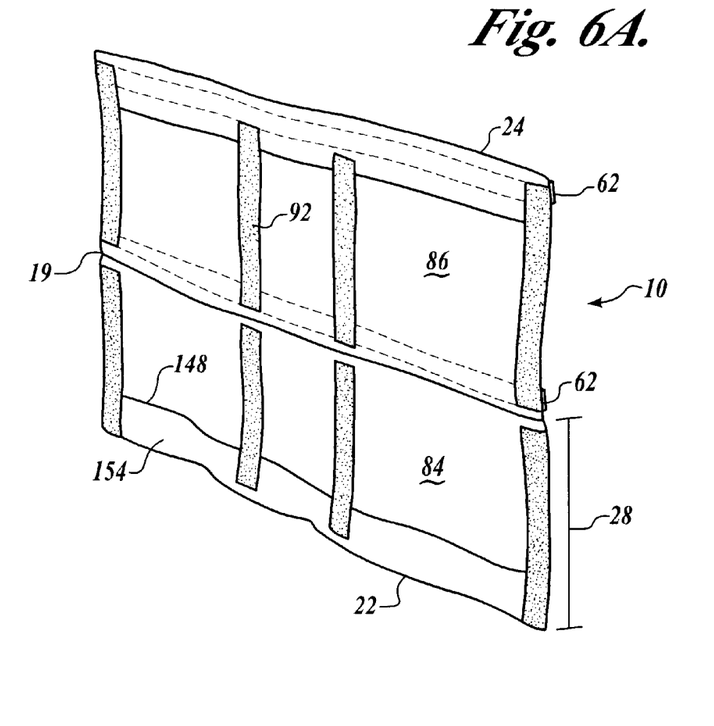
FIG. 6A provides an exploded perspective view of a surgical instrument storage pack employing the concepts of the invention and having a multiple pocket design.
Figure 6B:
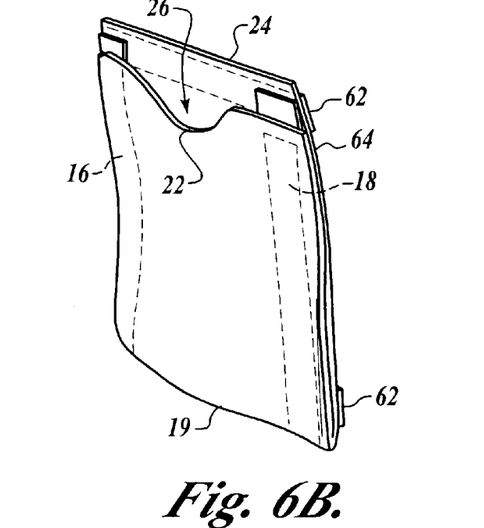
FIG. 6B provides a frontal perspective view of a surgical instrument storage pack employing the concepts of the invention and having a single pocket design.

The instrument pack of the invention provides excellent utility in a single pocket configuration (see, e.g., FIG. 6B). Preferably, the pack is configured with multiple instrument storage pockets 20, for example, two, three, four or five, pockets (see, e.g., FIGS. 4–6A).

In more detailed aspects of the invention, a standard instrument storage pack features a specific pocket depth dimension (bar 28, FIG. 6A) of between approximately 3.0 to 8.0 inches, more typically between about 4.5 to 6.5 inches, and preferably about 5.0 to 6.0 inches, whereby the pocket is adapted to receive standard surgical instruments in a manner that provides for secure insertion and storage of the instrument into the pocket, while enabling the surgeon or assistant to visualize and grasp an operating end 30 of the instrument extending above the front panel upper margin 22 (see, e.g., FIGS. 1 and 6A). A width dimension of the pocket (bar 32, FIG. 5) is between approximately 1.5 to 6.0 inches, more typically between about 2.0 to 5.0 inches, and preferably about 2.5 to 4.5 inches, thus configuring the pocket to securely yet removably receive multiple standard instruments.

The storage pack 10 of the invention incorporates a removable. adjustable attachment element for securely, removably and adjustably attaching the instrument storage pack to a frontal abdominal region 34 or chest region 36 of a surgeon's garment 38 or other article of surgical clothing covering the frontal abdominal and/or chest region of the surgeon. The attachment element is specifically adapted to securely maintain the instrument pack and instrument(s) within a sterile field approximately delineated at its upper height by the surgeon's clavicles 40 and an upper surface 42 of an operating table 44.

As illustrated in FIGS. 1–3, the attachment element may be in the form of a belt 46 or any other mounting or closure device that encircles or embraces a surgeon's or assistant's abdomen or chest or otherwise (e.g., by over-the-head or shoulder sling(s), strap(s), collar(s), harness(es), etc.) mounts the instrument pack to the individual's body to secure the pack in a frontal abdominal or chest position to maintain the pack and instruments reliably within the sterile operating field and provide easy access, including visual and manual access, to the instrument(s) stored in the pack pocket(s) 20. An exemplary attachment element comprises a belt 46, as illustrated in FIGS. 1–3, wherein the belt features opposing straps sized and dimensioned to comfortably and securely encircle the surgeon's or assistant's abdominal or lower chest region and engage one another, for example by opposing segments 52, 54 of hook and loop material, snaps, buckles, etc. The engaging element(s) mount on the straps capable of securing overlapping portions of the straps to one another. In this fashion, the belt or alternative mounting or closure device is adjustable to accommodate a range of body dimensions, e.g., a range of waist or chest circumferences among surgeons and assistants. The belt is attached to lateral margins 56, 58 of the pack, for example by stitching, gluing or otherwise affixing the straps to the lateral margins of the back panel 14 or other marginal structural element of the pack.

In alternative aspects of the invention, the pack is secured to a frontal abdominal or chest region of the surgeon's garment 38 without strap, sling or harness elements by removable attachment means which affix the pack directly to the chest or abdominal region of a surgeon's garment. Materials and devices for affixing the pack in this manner include, for example, one or more segment(s) (e.g., a patch or horizontal or vertical strip) of adhesive tape, film or gel 62 attached to a back surface 64 of the pack (see, e.g., FIG. 6B) which may be a back surface of the back panel 14 or a back surface of an additional layer of material integrated into the pack. In more detailed aspects, the pack is affixed to the surgical garment by an adhesive material such as an adhesive gel that firmly but removably engages a frontal surface of the garment. According to this aspect of the invention, the surgeon can mount the pack at any selected height suited to the surgeon's body dimensions to position the pack in the sterile field and provide secure storage and access to the instruments stored in the pack. The adhesive material is specifically adapted to affix the pack loaded with multiple instruments, for example 5–10 up to twenty or more standard instruments such as clamps and scissors, securely to a textile or paper surface of a surgical garment and to allow removal and reattachment of the pack to the garment. Accordingly, the surgeon can adjust the vertical and horizontal position of the pack for optimal use.

Figure 4:
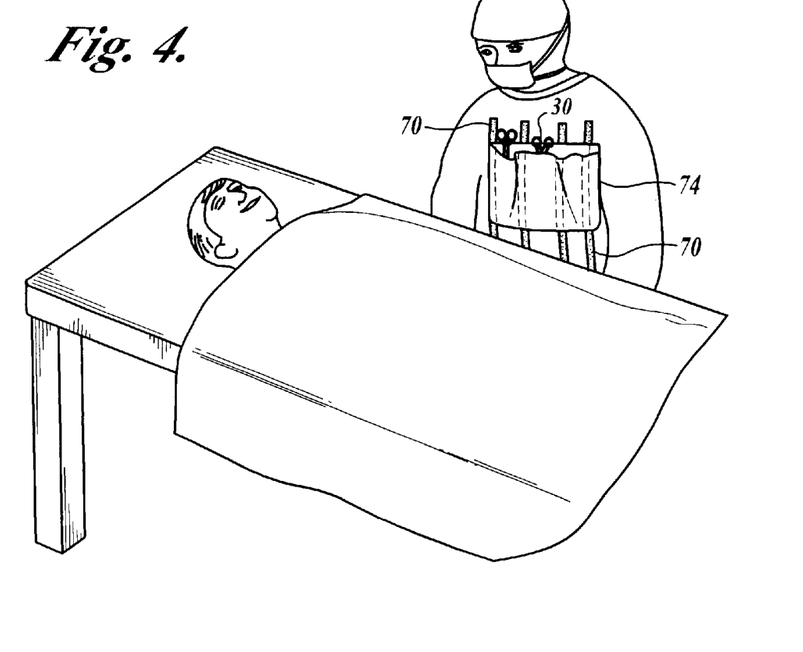
FIG. 4 is an environmental view showing a surgeon wearing a surgical instrument storage pack employing the concepts of the invention and mounted by an optional, vertically adjustable direct mounting mechanism.

Alternatively, one or more non-adhesive engaging elements connected to a back or lateral surface of the pack that engage(s) one or more complementary engaging element(s) on a surgical garment 38 can be provided to secure the pack in the region of the surgeon's chest or abdomen (see, e.g., FIGS. 4 and 5). In exemplary embodiments, the removable attachment means comprises complementary engaging elements, for example snaps, buckles, or opposing segments of hook and loop material, affixed to opposing surfaces of the pack and surgical garment. One such embodiment is depicted in FIGS. 4 and 5, wherein the complementary engaging element(s) that provide(s) a removable, adjustable attachment means includes one or more segment(s) of attaching hook or loop material 68 (e.g., Velcro) protruding from the back surface 64 of the storage pack. This attachment element is designed to engage one or more complementary segment(s) 70 of hook or loop material mounted on an abdominal or chest portion of the surgical garment and opposingly positioned and dimensioned to engage the one or more segment(s) of attaching hook or loop material protruding from the back surface of the pack. In the embodiment depicted in the Figures, the removable, adjustable attachment means includes a plurality of horizontal, elongate segment(s) of attaching hook or loop material 68 protruding from the back surface of the storage pack which are positioned and dimensioned to engage a plurality of vertical elongate segments 70 of complementary hook or loop material mounted on the frontal abdominal or chest portion of the surgical garment. According to this aspect of the invention, the pack can be vertically adjustably mounted to the abdominal or chest portion of the garment. The surgeon wearing the garment can thus mount the pack at an appropriate height adapted to the surgeon's individual body dimensions to position the pack in the sterile field and in such a manner as to allow easy visualization and access to the instruments stored in the pack. Likewise the surgeon can readily adjust the location of the pack for optimal use, for example, by changing a height position of the pack relative to the garment to achieve a better mounting position or to optimize storage and handling of different tools having different sizes and shapes. Preferably, there is at least one strip of hook and loop material adjacent and parallel to the upper margin 24 of the back panel 14, and more preferably at least a second strip adjacent and parallel to a lower margin 72 of the back panel, and sometimes three or four segments of attaching hook and loop material affixed to the back surface of the pack to securely attach the pack to the surgical garment. The garment in turn has at least one strip of complementary hook and loop material 70 positioned, e.g., above and/or below sternum height, to engage the attaching hook and loop material to mount the pack. In preferred embodiments there are at least two, more preferably three or four, vertical strips of complementary hook and loop material positioned to securely engage the attaching hook and loop material, for example, at lateral margins 74 of the back panel 14. As the artisan will readily appreciate, a comparable configuration of alternative complementary attachment elements (e.g., snaps, buckles, clips, or zipper segments) can be incorporated in the pack design to secure the pack in a correct, removable and adjustable position. A garment thus equipped with one or more complementary attachment elements for removably mounting an instrument storage pack to the garment is therefore yet an additional aspect of the invention.

In preferred aspects of the invention, the surgical instrument storage pack 10 is reusable (see, e.g., FIGS. 1–9) and is therefore necessarily adapted for sterilization before and after use. Other embodiments are disposable (see, e.g., FIGS. 10–11) but must nonetheless be introduced into the surgical theater in a sterile condition. Thus, prior to use the instrument pack of the invention is sterilized or manufactured under sterile conditions and thereafter packaged in a sterile container 80 (see, e.g., FIG. 11). The sterile container can be any sterile packaging system for medical devices and/or garments, for example a durable, sealed sterile bag, foil container, or plastic or other hard material box or sterile enclosure, and may be provided with additional safety features, for example an indicator label 82 to indicate that the package has been autoclaved, that a seal of the package has been broken, or that a shelf life of the instrument pack/container has exceeded a recommended pull date.

For ease of cleaning and sterilization, non-disposable instrument packs 10 of the invention are preferably designed to allow the front and back panels 12, 14 to be partially or completely detached from one another along at least one and preferably both of the vertical seams 16, 18. This permits at least partial manual separation of the front and back panels so that inner surfaces 84, 86 of the pockets (see, e.g., FIG. 3) can be exposed to cleaning tools and fluids to remove blood, tissue and other contaminants and to facilitate autoclaving or other sterilization procedures. In other preferred embodiments, the front and back panels of the instrument pack are detachable along all vertical seams and along the bottom seam 19 to allow complete manual separation of the front and back panels (see, e.g., FIG. 3) to facilitate cleaning and sterilization of the storage pack. Thus, in multipocketed embodiments of the storage pack (see, e.g., FIGS. 1–6a) which feature more than two vertical seams, for example a three pocketed design having a third vertical seam 88 and a fourth vertical seam 90, as shown in FIGS. 2 and 5, the panels are separable along all four vertical seams and along the bottom seam.

As with other attachment elements featured in the instrument storage pack of the invention, the panels can be separably joined by a variety of attachment devices, for example complementary hook and loop material, snaps, buttons, clips, zippers and the like. In preferred embodiments (see, e.g., FIG. 3), the panels are detachably joined together along the vertical seams 16, 18, 88, 90 by vertical segments or strips of hook and loop material 92 attached to the front and back panels 12, 14 and opposingly configured along at least a portion of the seam height. The attachment devices securely engage the front and back panels along the seams but allow for manual separation of the panels for improved cleaning and sterilization of the pack. Panel separation is further provided for by opposing horizontal attachment elements, e.g., horizontal segments or strips of hook and loop material 94, preferably attached along a lower, rear facing front panel edge 98 and slightly upwardly positioned parallel to a lower, rear facing back panel edge 98. In this manner, when the front and back panels are joined the lower front panel edge is folded a short distance upward against the lower, rear facing back panel edge 96 to engage the opposing horizontal segments of hook and loop material on the back panel slightly upward from the bottom seam 19. Thus, instruments in the pack do not impinge on the attachment elements so as to separate the panels, but instead impinge against a folded over edge (approximately marked by arrow 100 in FIGS. 2 and 3) of the front panel. For this purpose, the front panel may be more heavily constructed or reinforced in this portion of the panel to render the panel resistant to wear at the site where instruments impinge on the inner panel wall 84.

In other aspects of the invention, the pocket depth dimension 28 can be adjusted for enhanced ease and security of storage of instruments having different sizes and shapes. For example, the storage pack optionally includes means for adjusting a vertical position of the bottom seam 19 to raise or lower the position of the seam relative to one or both of the front and back panel upper margins 22, 24. Various configurations are contemplated to adjust the pocket depth in this manner. As shown in FIG. 3, one preferred embodiment provides for adjustment of the seam vertical position relative to the back pocket upper margin by increasing or decreasing the height of overlap of the lower rear facing edge 96 of the front panel 12 over the lower back facing edge 98 of the back panel 14. One design which achieves this relative adjustability of the front and back panels to change the bottom seam position features multiple attachment elements that secure the front and back panels positioned at different heights, for example at different heights along the back face of the back panel (or along the back surface 64 of the pack). As exemplified in FIG. 3, this may include a horizontal segment of hook and loop material 94 (or other alternative attachment element) positioned near the lower back facing edge of the back panel and a second horizontal segment of hook and loop material 110 attached to the rear surface of the back panel closer to the back panel upper margin. When the panels are separated along the bottom seam, the horizontal segment of hook and loop material attached along the lower rear facing edge of the front panel can be engaged to either the first or second horizontal segment of hook and loop material on back surface of the back panel during assembly—making the pocket deeper or shallower accordingly. Alternative engaging elements can of course be substituted for hook and loop materials, and additional engaging elements can be added at additional heights to increase the range of pocket depth adjustability.

As noted above, in some embodiments of the invention the instrument storage pack 10, 10' (see., e.g., FIGS. 10 and 11) is designed to be disposable. In preferred aspects, the pack is constructed of an inexpensive material that is compatible with surgical use. There are many compatible and suitable materials from which the panels 12, 14 of the pouch can be constructed, for example, a surgical grade kraft paper or polypropylene film. Another exemplary material is a disposable fabric as described in U.S. Pat. No. 4,196,245, issued to Kitson et al. on Apr. 1, 1980, incorporated herein by reference. One or more surfaces of the pack may be treated for water resistance or water proofing to prevent strike-thorough of liquids such as blood, treating fluids and other liquid materials normally encountered in the surgical theater. The material for constructing both disposable and non-disposable packs is also preferably resistant to caustic agents and disinfectants, for example, bleach, caustic detergents, phenol and quaternary ammonium materials commonly used as disinfectants in hospitals.

Figure 10:
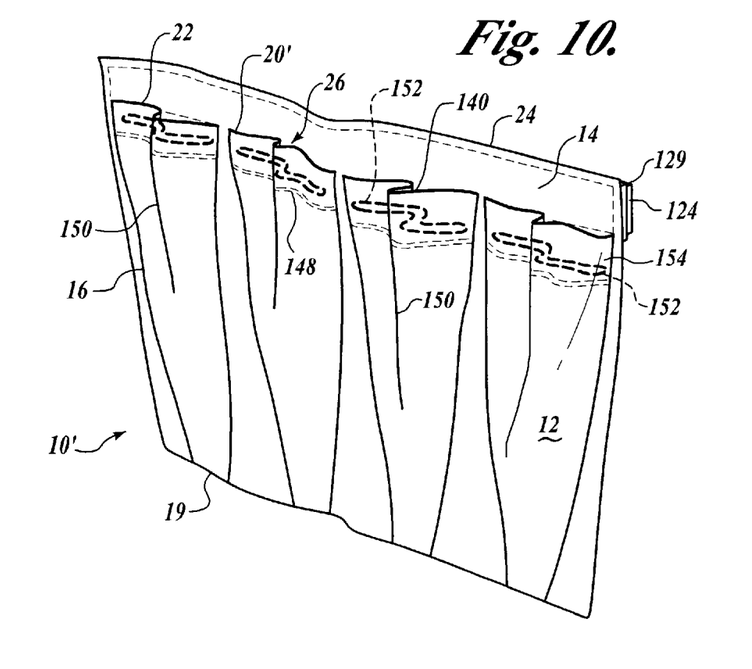
FIG. 10 provides a frontal perspective view of a videoscopic surgical instrument storage pack of the invention having a disposable construction.

All instrument packs 10, 10' of the invention may be provided in a disposable or reusable construction. Disposable packs may be provided as standard instrument packs or as packs adapted for receipt and storage of specialized videoscopic instruments. Preferably, disposable instrument packs are formed at least in part by joining the front and back panels 12, 14 permanently along the vertical pocket seams, e.g., seams 16, 18, 88, 90 and bottom seam 19 as shown in FIGS. 2 and 10, for example by stitching, gluing, stapling or other attachment means, to define the instrument pocket(s) 20. For ease of use and economy, the disposable pack is preferably mounted directly to the surgical garment by simple, low-cost engaging elements, such as one or more segments or strips of adhesive tape or gel. As exemplified by the disposable videoscopic instrument pack 10' shown in FIGS. 10 and 11, disposable packs will often incorporate at least two adhesive tape or gel strips 124 disposed at top and bottom margins 126, 128 of the pack. The adhesive material is preferably an adhesive gel compatible with medical use and adapted to securely but removably mount the pack to a surface of a surgical garment. The adhesive surface of the strips is preferably protected prior to use by a peel-off backing that can be manually stripped away to expose the adhesive surface at the time of use. The pack may be reinforced for durability and added strength of attachment, e.g., by folding over and gluing or stitching an edge 129 of the back panel near the top and/or bottom margin(s).

Non-disposable instrument packs of the invention are preferably constructed of a flexible, durable, autoclavable textile material that may be an organic or synthetic fabric or any other material compatible with the construction and use of the pack disclosed herein. Exemplary materials include woven and non-woven fabrics that may optionally be treated for water resistance or water proofing. Synthetic textile materials that are heat resistant and otherwise suited for autoclaving and use in the surgical theater include thermoplastic polymeric yarns, for example nylons, polyesters and the like. Preferred materials include polybutyl acetate and polyurethane fabrics. Desired characteristics of textile materials for use within the invention include "plastic memory", which is used to describe textile materials that can be stretched and heated repeatedly and which retain their original shape thereafter (see, e.g., U.S. Pat. No. 4,193,899, issued to Brenner et al.; U.S. Pat. No. 4,820,782, issued to Ueno; and U.S. Pat. No. 4,554,121, issued to Kramer et al., each incorporated herein by reference)

In preferred aspects of the invention, the surgical pack 10, 10' features pockets 20, 20' that are specially constructed to facilitate instrument insertion, storage and retrieval. In this context, the pockets may be designed to incorporate a deforming element that serves to deform at least a portion of the front panel upper margin 22 to cause at least partial spatial separation of the front panel upper margin from the back panel (i.e., at a point on the back panel opposing the front panel upper margin which collectively define the pocket opening 26 (see, e.g., FIGS. 2 and 10). In exemplary embodiments, the deforming element serves to impose an outwardly (i.e., frontally) convex configuration along at least part of the front panel upper margin to create an open pocket lip 140 where the front panel upper margin and back panel are separated. This opening can be observed and used as a point for unrestricted instrument insertion without the surgeon or assistant having to manually open the pocket first. To achieve this deformation, the front panel upper margin can be pleated, for example, by constructing the pockets with an upper width (bar 142 FIG. 3) of the front panel pocket member greater than a lower width (bar 144) of the front panel pocket member, while corresponding upper and lower width dimensions of the back panel pocket member are relatively closer in size (see, e.g., FIGS. 2 and 3; bar 146). Thus, when the pack is constructed or its seams are reassembled after cleaning, juxtapositioning and affixing of the front and back panel members, the front panel upper margin, having a width dimension greater than a corresponding width dimension between vertical pocket seams 16, 18, forces a pleated configuration that creates at least a partial pocket opening 140.

In more detailed embodiments, deformation of the pocket 20, 20' may be facilitated by reinforcing the upper pocket margin. As illustrated in FIGS. 3 and 10, this may be achieved in various ways, but most simply by having the front panel 12 fold over at the front panel upper margin 22 to form a double layer of material along the margin. A down-folded edge 148 is thereafter secured to an opposing, front panel inner surface 84, for example, by stitching, gluing, or interfacing. Thus reinforced, pleats 150 (see, e.g., FIG. 10) in the upper margin are stabilized. In addition, reinforcement of the upper front pocket edge in this manner reduces wear from tool insertion that is most likely to occur at this portion of the pack.

Yet another alternative means for deforming the pocket 20, 20' is to attach or invest one or more elongate stay elements 152 close to and paralleling the front panel upper margin 22. As illustrated in FIG. 10, a thin, flexible metal stay is preferably interposed between opposing, folded layers of the front panel 12, i.e., between the down-folded edge 148 of the front panel and the opposing, front panel inner surface 84, which are joined at least at the down-folded edge as described above to secure the stay element in position within a top seam 154 of the front panel. The stay element has sufficient rigidity that a user can bend the stay to deform the front panel upper margin into an outwardly convex configuration to create a pocket opening 26 which can be adjusted in size and shape. Thereafter, the selected opening size and shape will be maintained until reconfigured by the user. This design facilitates instrument insertion and also provides for more secure instrument storage, e.g., by enabling the user to adapt the pocket opening shape to engage an instrument more securely.

In yet another embodiment of the invention, the instrument pack 10 is modified as a specialized videoscopic instrument pack 10' (Long-InstruPak™) (see, e.g., FIGS. 7–10). The videoscopic instrument pack is designed to accommodate one or more elongate videoscopic, e.g., laparoscopic endoscopic and thoracoscopic, surgical instrument(s) 160. The videoscopic instrument pack is generally constructed as described above for the standard instrument pack. Accordingly, front and back panels 12, 14 of the pack define one or more pocket(s) 20' for secure receipt and storage of videoscopic instruments. Each pocket is specially designed to receive one or more videoscopic instruments through the pocket opening 26 that permits ready insertion of the instrument into the pocket and ready retrieval of the instrument therefrom.

Figure 7:
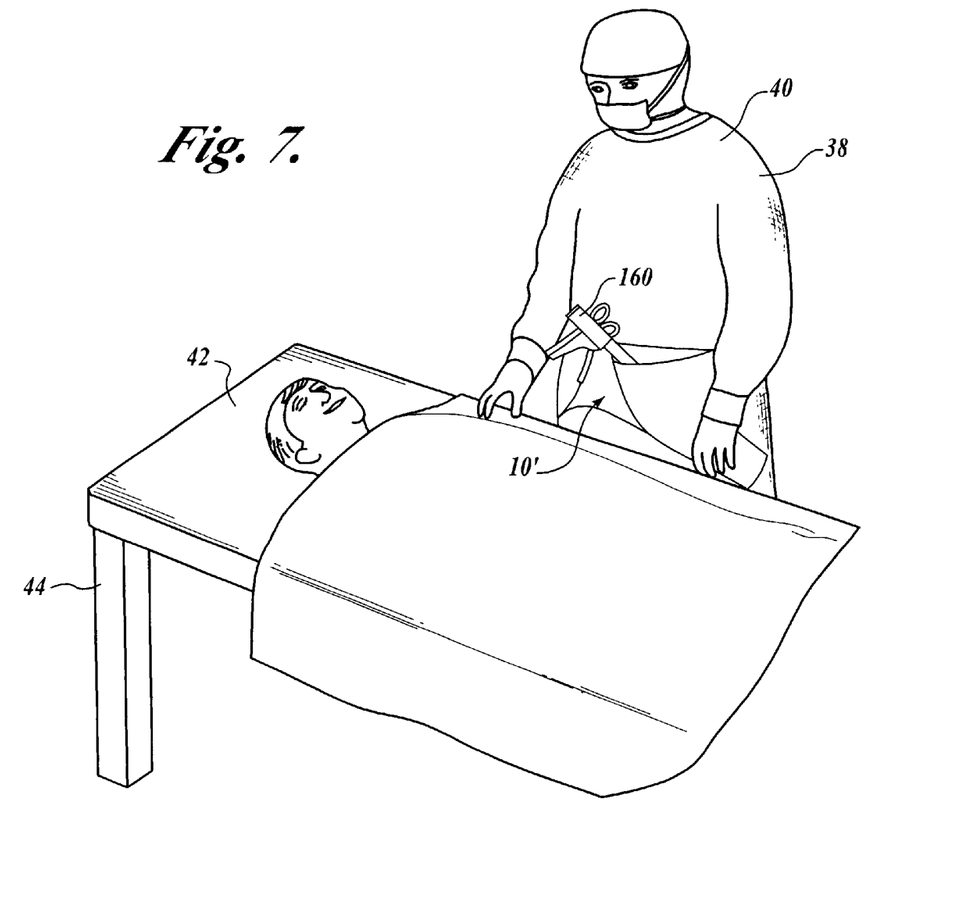
FIG. 7 is an environmental view showing a surgeon wearing a videoscopic surgical instrument storage pack employing the concepts of the invention and mounted by an optional belt design.
Figure 8:
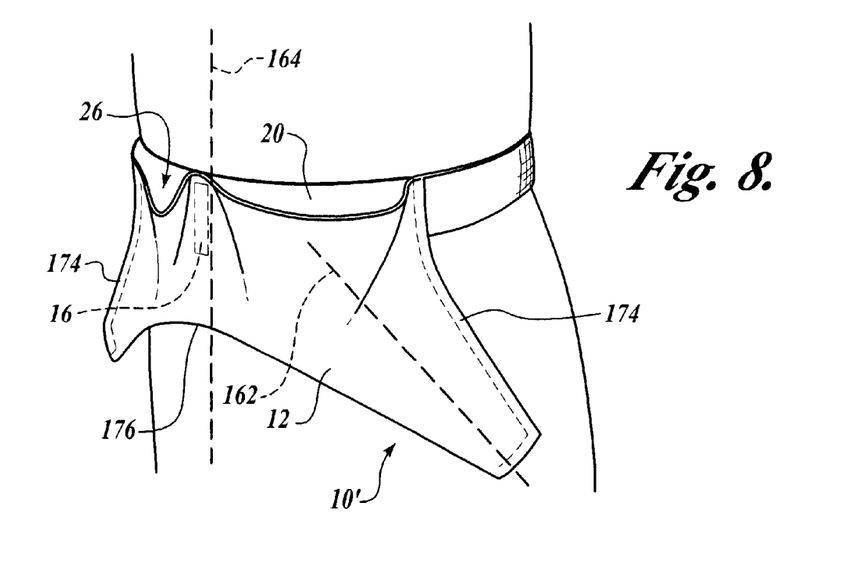
FIG. 8 provides a frontal perspective view of a videoscopic surgical instrument storage pack employing the concepts of the invention and having a reusable construction.
Figure 9:
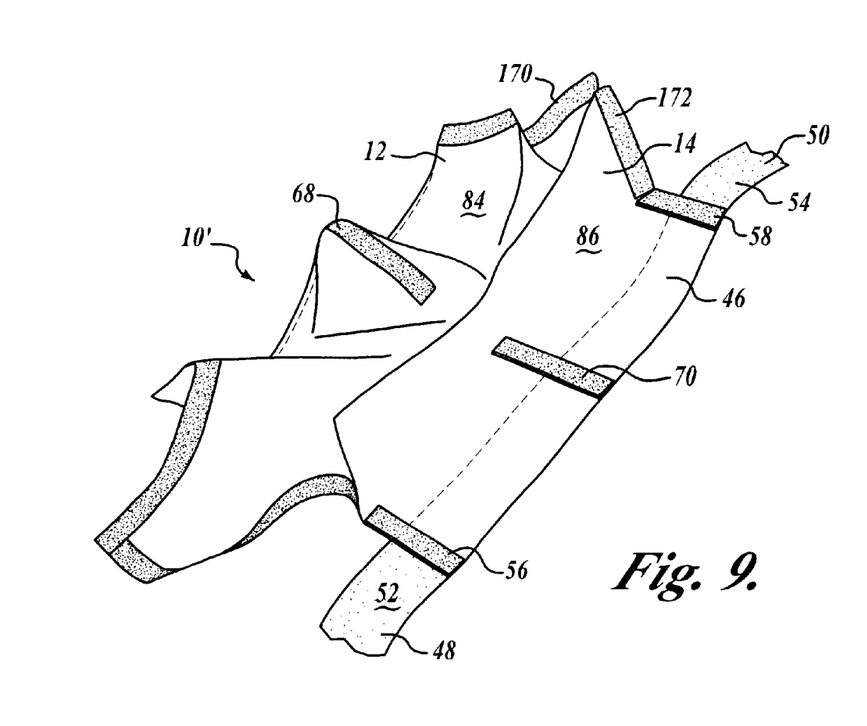
FIG. 9 provides an exploded perspective view of the videoscopic surgical instrument storage pack shown in FIG. 8.

As in the case of the standard instrument pack 10, the videoscopic instrument pack 10" may be removably mounted to the surgeon's abdominal or chest area in the manner of a belt, sling, harness or other mounting mechanism to secure the pack at a frontal abdominal position for ready access to the instruments (see, e.g., FIGS. 7–9). Alternatively, the pack can be secured to the frontal abdominal or chest region of a surgeon's garment directly, for example by adhesive strips 124 (see, e.g., FIGS. 10 and 11) or other engaging elements such as snaps, buckles, or opposing segments of hook and loop material, as described above.

Laparoscopic surgery utilizes a camera and long tools (about 18 cm) inserted through multiple small (about 1.5 cm) incisions in the abdomen to perform operations which are observed in real-time on a video monitor. Likewise, thoracoscopy involves the same method and similar tools as laparoscopy, but is performed through the chest wall within the thoracic cavity. Mediastinoscopy also involves the same method and similar tools as laparoscopy, but is performed through the chest wall within the mediastinum. Encoscopy utilizes a lighted flexible scope with a camera on the end, which is then inserted via the oral cavity or anal orifice to view the upper and lower intestinal tracts, respectively. As surgical techniques and experience with video-assisted procedures evolve, surgeons are learning to perform more advanced videoscopic operations—operations which before 1990 were exclusively performed as open procedures.

The handling of videoscopic instruments is a relatively new task for every surgeon and surgical assistant because the videoscopic technique has rapidly expanded only in the last decade. Learning to transfer and receive long, thin, awkward instruments differs tremendously from the passage of traditional instruments used during open procedures. Videoscopic instruments are not readily received from the surgical assistant who must avoid handing tools over the surgeon's shoulder or below waist level in an effort to maintain sterility. Safely returning instruments within the sterile field from a surgeon to the assistant is also challenging, and particularly inefficient when the same instrument will be needed again shortly after its return.

The videoscopic instrument pack 10' eliminates the need for a surgeon to verbally request certain tools. An instrument which is repetitively but not continuously used throughout a case, for example a harmonic scalpel, grasper, suction, hook, or spatula, can be grasped from the surgeon's instrument pack and put to use immediately. The surgeon thus maintains better attention on the surgical field for a more significant amount of uninterrupted time, especially when commonly used tools are stored in the instrument pack.

The primary departure of the videoscopic instrument pack 10' from the design and construction of the standard instrument pack 10 relates to the configuration and structure of the instrument storage pocket(s) 20'. In detailed aspects, the videoscopic instrument pack has front and back panels 12, 14 that define one or more generally V-shaped pocket(s) to securely and easily receive and store videoscopic instruments. The front and back panels are joined at vertical seams that are oriented downwardly toward a pocket midline axis 162 (see, e.g., FIGS. 8 and 11). By virtue of this design, videoscopic instruments that typically have a narrow tip and wider gripping end, often including a handle or other control element, are readily accommodated within the pocket and securely engaged therein. In other detailed aspects, the pocket(s) of the videoscopic instrument pack are themselves angled downward transversely away from a midline axis 164 of the pack, whereby the tip of the instrument 160 stored in the pocket extends downward transversely away from a midline of a surgeon wearing the pack and the gripping end of the instrument is situated in a proximate to medial position to facilitate storage and retrieval of the instrument (see, e.g., FIGS. 8 and 9).

In embodiments of the videoscopic instrument pack 10', the pack is conveniently worn as a belt or holster type pack, whereby the pack is mounted around the waist with the instrument storage pocket(s) situated in the frontal abdominal region 34 of the wearer, as described above. In the embodiment shown in FIGS. 8 and 9, the pack is reusable and the front and back panels 12, 14 are partially or completely separable, for example, by uncoupling one or more complementary engaging elements opposingly positioned on the front and back panels along the margins of the pockets. For example, the pack shown in FIGS. 8 and 9 have vertical attaching and complementary segments or strips of hook and loop material 68, 70 opposing one another on the front and back panels extending along one or more vertical seam(s) 16, and marginal attaching and complementary segments or strips of hook and loop material 170, 172 opposing one another on the front and back panels extending along one or more marginal seams 174. Separation of these engaging elements allows partial separation of the front and back panels so that their respective inner surfaces 84, 86 can be exposed to cleaning implements and fluids for sterilization and use. In alternative embodiments, the front and back panels can be made partially or completely separable. For example, the front and back panels can be non-detachably joined along a bottom pack margin 176 (e.g., by gluing or stitching), or the panels can also be joined at this margin by detachable engaging elements as described above to allow complete panel separation.

Figure 11:
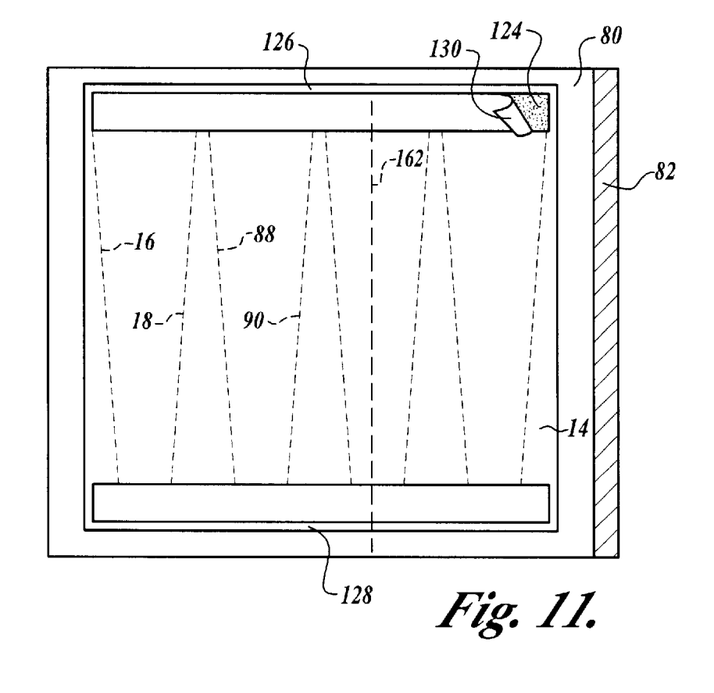
FIG. 11 is a rear plan view of the disposable videoscopic surgical instrument storage pack shown in FIG. 10.

As illustrated in FIGS. 10 and 11, the videoscopic instrument pouch 10' is also provided in the form of a disposable pouch, generally incorporating the features of the standard, disposable instrument pouch but including the specific features described above with respect to pocket design and other design features adapted to storage and retrieval of videoscopic instruments. As with the standard pouch, the disposable videoscopic instrument pouch has a simple, inexpensive construction of disposable textile material such as surgical grade paper. It can have one to several pockets 20' and is preferably mounted to the surgical garment 38 by removable mounting means, preferably adhesive tape or gel strips 124 as described above. Also optionally included in the videoscopic instrument pack are pocket reinforcing elements, e.g., a multiple-layer front pocket upper margin 22 and/or a pocket deforming element such as a pleat 150 or stay 152.

Although the invention has been described in exemplary detail by way of the foregoing description and accompanying Figures, it will be evident to those skilled in the art that certain modifications can be made to the subject matter disclosed herein without departing from the spirit and scope of the appended claims.

What is claimed is:

1. A surgical instrument storage pack for retaining instruments in a surgical field comprising:

a front panel and back panel joined along first and second vertical seams and along a bottom seam to define an instrument-retaining pocket, said front and back panels having opposing upper margins defining a pocket opening, said pocket and pocket opening sized and dimensioned to removably receive and securely store one or more surgical instruments; and removable, adjustable attachment means for securely, removably and adjustably attaching the instrument storage pack adjacent a frontal abdominal or chest region of a surgeon or surgical assistant to securely maintain the instrument pack and instrument(s) within a sterile field, wherein said removable, adjustable attachment means includes a segment of adhesive tape, film or gel protruding from a back surface of said storage pack to firmly mount the pack to a frontal abdominal or chest region of the surgeon's or surgical assistant's garment to securely maintain the instrument pack and instrument(s) within the sterile field.

2. The surgical instrument storage pack according to claim 1, wherein the front and back panels are joined along said first and second vertical seams by interlocking hook and loop material affixed to opposing front and back panel vertical seam edges and wherein the front and back panels are detachable along said first and second vertical seams to allow at least partial manual separation of the front and back panels to facilitate cleaning and sterilization of the storage pack.

3. The surgical instrument storage pack of claim 2, wherein the front and back panels are detachable along said first and second vertical seams and along said bottom seam to allow complete manual separation of the front and back panels to facilitate cleaning and sterilization of the storage pack.

4. The surgical instrument storage pack according to claim 1, wherein the front and back panels are detachable and adjustably reattachable along said bottom seam to allow manual separation and relative height adjustment of the front and back panels to adjust a depth dimension of the instrument-retaining pocket.

5. The surgical instrument storage pack of claim 4, wherein the front and back panels are detachable along said first and second vertical seams and along said bottom seam to allow complete manual separation of the front and back panels to facilitate cleaning and sterilization of the storage pack.

6. The surgical instrument storage pack of claim 4, wherein the front and back panels are detachable and adjustably reattachable along said bottom seam by opposing horizontal attachment elements to allow manual separation and relative height adjustment of the front and back panels to adjust a depth dimension of the instrument-retaining pocket.

7. The surgical instrument storage pack of claim 2 or 4, wherein the front and back panels are constructed of an autoclavable textile material.

8. The surgical instrument storage pack according to claim 1, wherein the front and back panels are constructed of a disposable, surgical grade paper material.

9. The surgical instrument storage pack of claim 1, wherein the removable, adjustable attachment means comprises a segment of sterile adhesive gel.

10. The surgical instrument storage pack of claim 1, wherein all surfaces of the instrument storage pack are aseptic and free of toxic or caustic agents.

11. A surgical instrument storage pack according to claim 1, in combination with a closed sterile package sized and dimensioned to sealably enclose said pack, wherein said pack is sterilized and enclosed within said package.

12. The surgical instrument storage pack of claim 11, wherein the front and back panels are constructed of a disposable, surgical grade paper material.

13. The surgical instrument storage pack of claim 1, wherein said upper margin of said front panel incorporates a manually deformable pleat or stay to maintain at least a portion of said upper margin of said front panel in an outwardly deformed disposition relative to said back panel upper margin to facilitate insertion of surgical instruments into said pocket and to provide for adjustability of both size and shape of the pocket opening to securely engage said instrument(s) within said pocket opening.

14. A surgical instrument storage pack according to claim 1 wherein said front panel and back panel are joined along said first and second vertical seams to define a V-shaped laproscopic instrument-retaining pocket, said front and back panels having opposing upper margins defining a pocket opening, wherein said pocket and pocket opening are sized and dimensioned to removably receive and securely store one or more laproscopic surgical instruments, and wherein the front and back panels are joined along said first and second vertical seams which are oriented downwardly converging toward a midline axis of the pocket.

15. The surgical instrument storage pack of claim 14, wherein said front panel upper margin incorporates a manually deformable pleat or stay to maintain at least a portion of said upper margin of said front panel in an outwardly deformed disposition relative to said back panel upper margin to facilitate insertion of surgical instruments into said pocket and to provide for adjustability of both size and shape of the pocket opening to securely engage said instrument(s) within said pocket opening.

16. The surgical instrument storage pack of claim 14, wherein the front and back panels are joined along said first and second vertical seams by interlocking hook and loop material affixed to opposing front and back panel vertical seam edges and wherein the front and back panels are detachable along said first and second vertical seams to allow at least partial manual separation of the front and back panels to facilitate cleaning and sterilization of the storage pack.

17. The surgical instrument storage pack of claim 14, wherein said front and back panels are joined along at least three front and back panel vertical seams to define a plurality of instrument-retaining pockets.

18. The surgical instrument storage pack of claim 14, wherein said front and back panels are joined along vertical seams to define one or more V-shaped laproscopic instrument-retaining pocket(s) which is/are oriented transversely away from a midline axis of the pack, whereby a tip of said laparoscopic instrument(s) stored in the pocket(s)

extends downwardly transversely away from the midline with a gripping end of the instrument situated near the midline to facilitate storage and retrieval of the instrument.

19. The surgical instrument storage pack of claim 1, wherein a width dimension of said pocket is between approximately 2.5 to 6.5 inches.

20. The surgical instrument storage pack of claim 1, further comprising pocket depth adjustment means to adjust a depth dimension of said pocket.

21. The surgical instrument storage pack of claim 1, wherein the front and back panel bottom seam can be vertically repositioned to adjust a depth dimension of said pocket.

22. A surgical instrument storage pack for retaining instruments in a surgical field comprising:

a front panel and back panel joined along first and second vertical seams and along a bottom seam to define an instrument-retaining pocket, said front and back panels having opposing upper margins defining a pocket opening, said pocket and pocket opening sized and dimensioned to removably receive and securely store one or more surgical instruments, wherein the front and back panels are detachable and adjustably reattachable along said bottom seam to allow manual separation and relative height adjustment of the front and back panels to adjust a depth dimension of the instrument-retaining pocket; and removable, adjustable attachment means for securely, removably and adjustably attaching the instrument storage pack adjacent a frontal abdominal or chest region of a surgeon or surgical assistant to securely maintain the instrument pack and instrument(s) within a sterile field, wherein he front and back panels are detachable and adjustably securing a lower, front panel edge in an upwardly-folded position against a rear surface of the back panel.

23. A surgical instrument storage pack for retaining instruments in a surgical field comprising:

a front panel and back panel joined along first and second vertical seams and along a bottom seam to define an instrument-retaining pocket, said front and back panels having opposing upper margins defining a pocket opening, said pocket and pocket opening sized and dimensioned to removably receive and securely store one or more surgical instruments, wherein the front and back panels are joined along said first and second vertical seams by interlocking hook and loop material affixed to opposing front and back panel vertical seam edges and wherein the front and back panels are detachable along said first and second vertical seams to allow at least partial manual separation of the front and back panels to facilitate cleaning and sterilization of the storage pack; and removable, adjustable attachment means for securely, removably and adjustably attaching the instrument storage pack adjacent a frontal abdominal or chest region of a surgeon or surgical assistant to securely maintain the instrument pack and instrument(s) within a sterile field, wherein said removable, adjustable attachment means includes one or more segment(s) of hook or loop material protruding from a back surface of said storage pack.

24. A surgical instrument storage pack for retaining instruments in a surgical field comprising:

a front panel and back panel joined along first and second vertical seams and along a bottom seam to define an instrument-retaining pocket, said front and back panels having opposing upper margins defining a pocket opening, said pocket and pocket opening sized and dimensioned to removably receive and securely store one or more surgical instruments, wherein the front and back panels are joined along said first and second vertical seams by interlocking hook and loop material affixed to opposing front and back panel vertical seam edges and wherein the front and back panels are detachable along said first and second vertical seams to allow at least partial manual separation of the front and back panels to facilitate cleaning and sterilization of the storage pack; and removable, adjustable attachment means for securely, removably and adjustably attaching the instrument storage pack adjacent a frontal abdominal or chest region of a surgeon or surgical assistant to securely maintain the instrument pack and instrument(s) within a sterile field, further comprising a surgical garment having complementary attachment means that allow for adjustable mounting of the storage pack to either an abdominal or chest portion of said garment.

25. The surgical instrument storage pack of claim 24, wherein said removable, adjustable attachment means includes a plurality of horizontal, elongate segment(s) of hook or loop material protruding from said back surface of the storage pack and wherein said complementary attachment means of said surgical garment includes a plurality of segments of vertical, elongate hook or loop material mounted on both the abdominal and chest portions of said garment, whereby said pack can be vertically adjustably mounted to either said abdominal or chest portion of said garment.

26. A laproscopic surgical instrument storage pack for retaining laproscopic instruments in a surgical field comprising:

a front panel and back panel joined along first and second vertical seams to define a V-shaped laproscopic instrument-retaining pocket, said front and back panels having opposing upper margins defining a pocket opening, said pocket and pocket opening sized and dimensioned to removably receive and securely store one or more laproscopic surgical instruments, wherein the front and back panels are joined along said first and second vertical seams which are oriented downwardly converging toward a midline axis of the pocket; and removable, adjustable attachment means for securely, removably and adjustably attaching the instrument storage pack adjacent a frontal abdominal or chest region of a surgeon or surgical assistant to securely maintain the instrument pack and instrument(s) within a sterile field, further comprising a surgical garment having complementary attachment means that allow for adjustable mounting of the storage pack to either an abdominal or chest portion of said garment.

27. The laproscopic surgical instrument storage pack of claim 26, wherein said removable, adjustable attachment means includes a plurality of horizontal, elongate segment(s) of hook or loop material protruding from said back surface of the storage pack and wherein said complementary attachment means of said surgical garment includes a plurality of segments of vertical, elongate hook or loop material mounted on both the abdominal and chest portions of said garment, whereby said pack can be vertically adjustably mounted to either said abdominal or chest portion of said garment.

* * * * *